United States Patent [19]

Cohen et al.

[11] 4,095,103

[45] June 13, 1978

[54] APPARATUS AND METHOD FOR DETERMINATION OF RESIDUAL STRESS IN CRYSTALLINE SUBSTANCES

[75] Inventors: Jerome B. Cohen, Glencoe, Ill.; Michael R. James, Groningen, Netherlands

[73] Assignee: Northwestern University, Evanston, Ill.

[21] Appl. No.: 819,985

[22] Filed: Jul. 28, 1977

Related U.S. Application Data

[63] Continuation-in-part of Ser. No. 666,393, Mar. 12, 1976, abandoned.

[51] Int. Cl.² .......................................... G01N 23/20
[52] U.S. Cl. .............................. 250/277 CH; 250/272; 250/273
[58] Field of Search ........ 250/272, 273, 277, 277 CH, 250/278, 374, 385

[56] References Cited

U.S. PATENT DOCUMENTS

| | | | |
|---|---|---|---|
| 2,386,785 | 10/1945 | Friedman | 250/273 |
| 3,011,060 | 11/1961 | Borenbosch et al. | 250/272 |
| 3,126,479 | 3/1964 | Mattson | 250/272 |
| 3,402,291 | 9/1968 | Weinman | 250/277 |
| 3,483,377 | 12/1969 | Borkowski et al. | 250/374 |
| 3,517,194 | 6/1970 | Borkowski et al. | 250/385 |
| 3,617,705 | 11/1971 | Takano et al. | 250/273 |
| 3,934,138 | 1/1976 | Bens | 250/272 |

*Primary Examiner*—Alfred E. Smith
*Assistant Examiner*—B. C. Anderson
*Attorney, Agent, or Firm*—Kegan, Kegan & Berkman

[57] ABSTRACT

Apparatus and method for determination of residual stress in crystalline substances. An X-ray source is focused at two different, preselected angles with respect to a surface of a substance, and X-ray diffraction peaks are located with a single position-sensitive X-ray detector. The apparatus has positioning probes affixed to a base for maintaining the base in fixed relationship with the substance, and an arcuate glide channel formed in the base for controlled angular shifting of the X-ray source and detector. Residual stresses are determined more quickly than with prior art methods and apparatus having comparable precision because only a single detector is used, and because the detector locates diffraction peaks without time-consuming diffractometer shifting.

7 Claims, 6 Drawing Figures

APPARATUS AND METHOD FOR DETERMINATION OF RESIDUAL STRESS IN CRYSTALLINE SUBSTANCES

The Government has rights in this invention pursuant to Contract No. N 00014-75-C-0580 awarded by the Office of Naval Research.

BACKGROUND OF THE INVENTION

This application is a continuation-in-part of copending application Ser. No. 666,393 filed Mar. 12, 1976, abandoned.

The present application relates to measurement of residual stresses in crystalline substances such as metals, ceramics, organic crystals and the like. More particularly, this invention is directed to an apparatus and method for determination of residual stresses with high precision, by location of two X-ray diffraction peaks in a single position-sensitive X-ray detector at two exposures of a substance to an X-ray source.

Several different types of apparatus and techniques are known in the prior art for determination of residual stresses in metals and other crystalline substances by measurement of variations in X-ray diffraction patterns. However, each of these prior art techniques and apparatus suffers from one or more serious disadvantages making it either less precise, more time-consuming, or both less precise and slower than the apparatus and method of the present invention.

The need for portable apparatus for determination of residual stresses in crystalline substances by measurement of variations in X-ray diffraction patterns has been recognized in the prior art. However, until the present invention, no apparatus had been developed which is sufficiently lightweight, compact, precise, and quick to be made truly portable for onsite residual stress determinations. Each of the types of prior art apparatus has been deficient in at least one of the properties mentioned.

Instruments in the field of X-ray diffraction stress analysis have usually been based on modifications and innovations associated with or built around a diffractometer. The Fastress (1) unit utilizes two X-ray tubes and two pairs of detectors to locate the peak, one pair each at $\Psi=0°$ and at $\Psi=45°$. Both peak positions are found by matching the intensity in each detector with its mate, which is positioned on the other side of the profile. The midpoint between the two detectors is used for the peak location. Both pairs of detectors are calibrated in terms of angular position so the peak shift can be electronically determined, assuming the diffraction profile is symmetric and the detector efficiencies are matched. Reproducibility is about ±20 MPa in a 3 minute test on hardened steel samples. The device is semi-portable in that the measuring head (incorporating the X-ray tube, detectors and $2\theta$ motion), electronics and power supply may be rolled on a cart in the laboratory.

(1) E. W. Weinman, J. E. Hunter, and D. D. McCormack, Determining Residual Stress Rapidly, 96 Metal Progress 88(1969).

Another dedicated unit, the Shimadzu X-ray Diffraction stress analyzer, (2) uses normal scanning of the profile to locate the peak. Two peaks at different $\Psi$ inclinations may be scanned at once using two X-ray tubes and two detectors mounted on one goniometer head. The device is capable of $sin^2\Psi$ analysis but uses a separate calculator to determine the stress.

(2) K. Kamachi, X-Ray Study on Strength and Deformation of Metals, The Society of Materials Science, Japan (1971), p.95

More recently, Compagnie General de Radiologie of Paris, France has developed and begun manufacturing an instrument incorporating two separate position-sensitive X-ray detectors (3). Changes in diffraction angle are measured relative to an unstressed first specimen of the same material as the body whose stress is measured. In addition, the instrument must be calibrated using a second specimen subjected to a known stress. While this procedure is accurate, it is so time consuming that the single exposure method of analysis is used. The manufacturer of the Bens instrument claims that residual stress measurements may be made in 15 minutes with a precision of ± 300 bars (4400 psi). In contrast, it has been found that similar precision can be obtained with the method and apparatus of the present invention in only about 4 to 20 seconds.

(3) J. Bens, U.S. Pat. No. 3,934,138 issued Jan. 20, 1976

The reduction in measurement time with the present invention compared with the method and apparatus of the Bens patent is unexpected in view of the fact that applicants perform two diffraction angle measurements successively with only a single detector whereas Bens makes two diffraction angle measurements simultaneously with two separate detectors. Superficially it would appear that applicants' method is inherently slower as they perform an additional step, but such is not the case. Because of the discrepancy between apparent disadvantages of applicants' method and actually observed advantages over Bens, a detailed explanation is provided below as to how applicants' invention enables them to achieve greater speed for comparable precision in spite of their additional method step.

The general equation for measurement of stress by X-ray diffraction is:

$$\sigma\phi = k(2\theta. - 2\theta_{10s})$$

where $2\theta$ and $2\theta_\Psi$ are values of the diffraction angle without and with a tilt by an angle $\Psi$ of the X-ray source to the surface of the crystalline substance. In applicants' method, $$k = \frac{1}{2} \frac{\pi}{180} \left( \frac{E}{1+v} \frac{1}{sin^2 \Psi} \right) cot \frac{1}{2} (\theta_0 + \theta_\Psi)$$

where E and $v$ are elastic constants.

Based upon equations reported by Norton (4) the value of $k$ in the two-detector method practiced by Bens is:

$$k_{Bens} = \frac{1}{4} \frac{\pi}{180} \frac{E}{1+v} \frac{cot \frac{1}{2}(\theta_o + \theta_\Psi)}{sin \theta \, sin 2\beta \, cos\theta}$$

where $\beta$ is the angle between normal to the surface of the specimen and the incident beam.

Dividing the first of the above equations by the second, $$\frac{k \text{ applicants}}{k \text{ Bens}} = \frac{2 \, sin \, \theta \, cos \, \theta \, sin \, 2\beta}{sin^2 \Psi}$$

For typical steel values, $\beta = \Psi = 45°$ and $\theta = 78°$ so that $$\frac{k \text{ applicants}}{k \text{ Bens}} = 2 \frac{(0.98)(0.21)(1)}{(0.5)} = 0.82$$

Because applicants $k$ is smaller than Bens' $k$ by a factor of 0.82, their method is more precise by a factor of $(1/0.82) = 1.22$.

(4) J. T. Norton, X-Ray Stress Measurement by the Single-Exposure Technique, 11 Adv. in X-Ray Analysis 401 (1967)

FIG. 6 of the drawings of the present application compares values of $k$ as a function of diffraction angle for the method of the invention and for the single exposure technique relied upon by Bens. The value of $k$ is significantly lower at all diffraction angles between 75° and 83° for applicants' method compared with the single exposure technique. In other words, the additional method step (e) recited in claim 1 and distinguishing applicants' invention from the Bens patent results in greater precision which eventually reduces the total measurement time compared with Bens and other prior art methods.

Because the two-detector Bens method is inherently less precise than the single detector method of the present invention, counting errors becomes more important in his method and longer data collection times are required. That is an important reason for the difference between the 15 minute measurement time claimed for the Bens apparatus, and the 4 to 20 second measurement time of the present invention for comparable precision.

Although the Bens patent mentions the desirability of making portable an X-ray diffraction stress detector, his apparatus is not truly portable. Instruments produced under the Bens patent use a water cooled X-ray tube requiring a heavy generator, and the electronics are not miniaturized. The apparatus is much too heavy and cumbersome for on-site residual stress determinations.

SUMMARY OF THE INVENTION

The present invention comprises a method for residual stress analysis and apparatus for practice of the method. Residual stress analyses are accomplished with speeds unequalled by any prior art methods or apparatus having comparable precision. A precision of ± 5000 psi can be achieved in only 4–20 seconds on hard and soft steel specimens.

The method and apparatus of the invention are adaptable to either the two-tilt or $\sin^2 \Psi$ techniques of X-ray diffraction residual stress analysis. Because all $2\theta$ movement is eliminated, no diffractometer is needed and the invention is adaptable to portable instruments. In addition, stresses in two or more directions or in two phases can be measured simultaneously in some instances.

It is a principal object of the present invention to provide a method and apparatus for rapid determination of residual stress in crystalline substances by locating X-ray diffraction peaks with a single position-sensitive X-ray detector.

It is a related object of the present invention to provide a method for residual stress analysis in which only a single X-ray detector is needed, thereby increasing the precision and reducing the time required for stress determinations.

Another object of the present invention is to provide a compact, light weight design for portable apparatus for residual stress analysis.

A further object of the invention is to provide method and apparatus for simultaneously determining residual stress in two or more directions or two or more phases of a crystalline substance.

These and other objects of the present invention are accomplished by positioning an X-ray source to direct a beam toward the principal surface of a substance being tested. X-rays are diffracted by the substance and the angle of diffraction is measured with a position-sensitive X-ray detector. In the preferred embodiment described herein the X-ray detector is a position-sensitive proportional counter (PSPC) in which X-rays cause a multiplicity of ionizing events having a peak corresponding to a diffraction angle of the substance. These ionizing events give rise to a pair of voltage pulses traveling in opposite directions in a high-resistance collecting element in the detector. The respective rise times of the two pulses are determined electronically, thereby indicating positions of ionizing events occurring within the detector. Diffraction peaks are located by calibrating the instrument to correlate positions of ionizing events with X-ray diffraction angles, and by analytically locating positions of peak incidence of ionizing events.

The X-ray source and detector are rotated by a predetermined angle and a second diffraction peak is located. Residual stress is then calculated by applying formulae derived from linear isotropic theory.

BRIEF DESCRIPTION OF A PREFERRED EMBODIMENT

Figure 1:
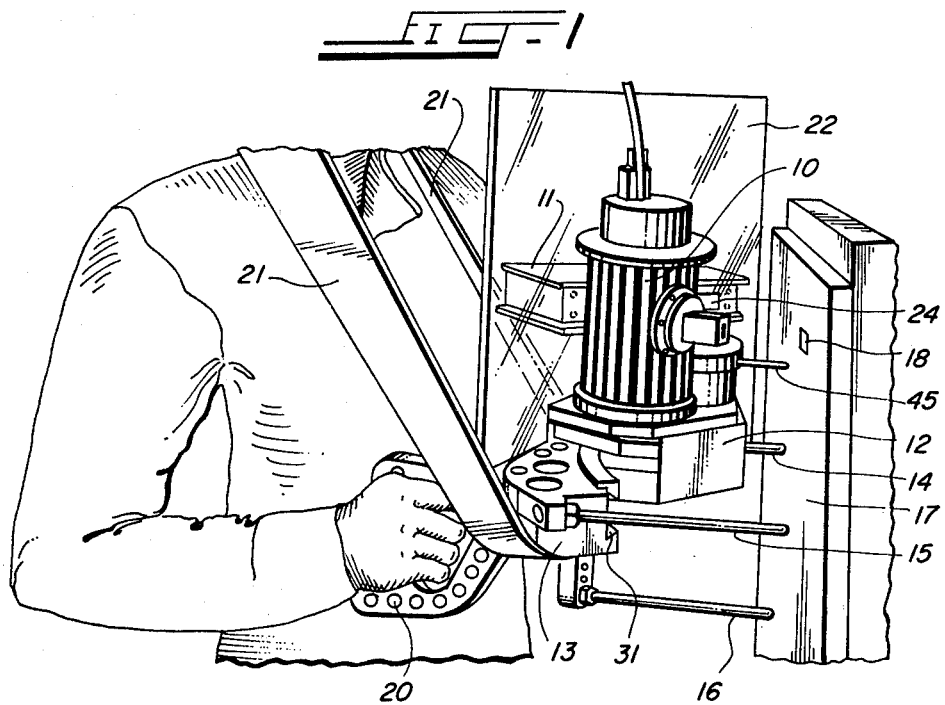
FIG. 1 is a side perspective view of the apparatus of the invention being used to perform an on-site residual stress determination.
Figure 2:
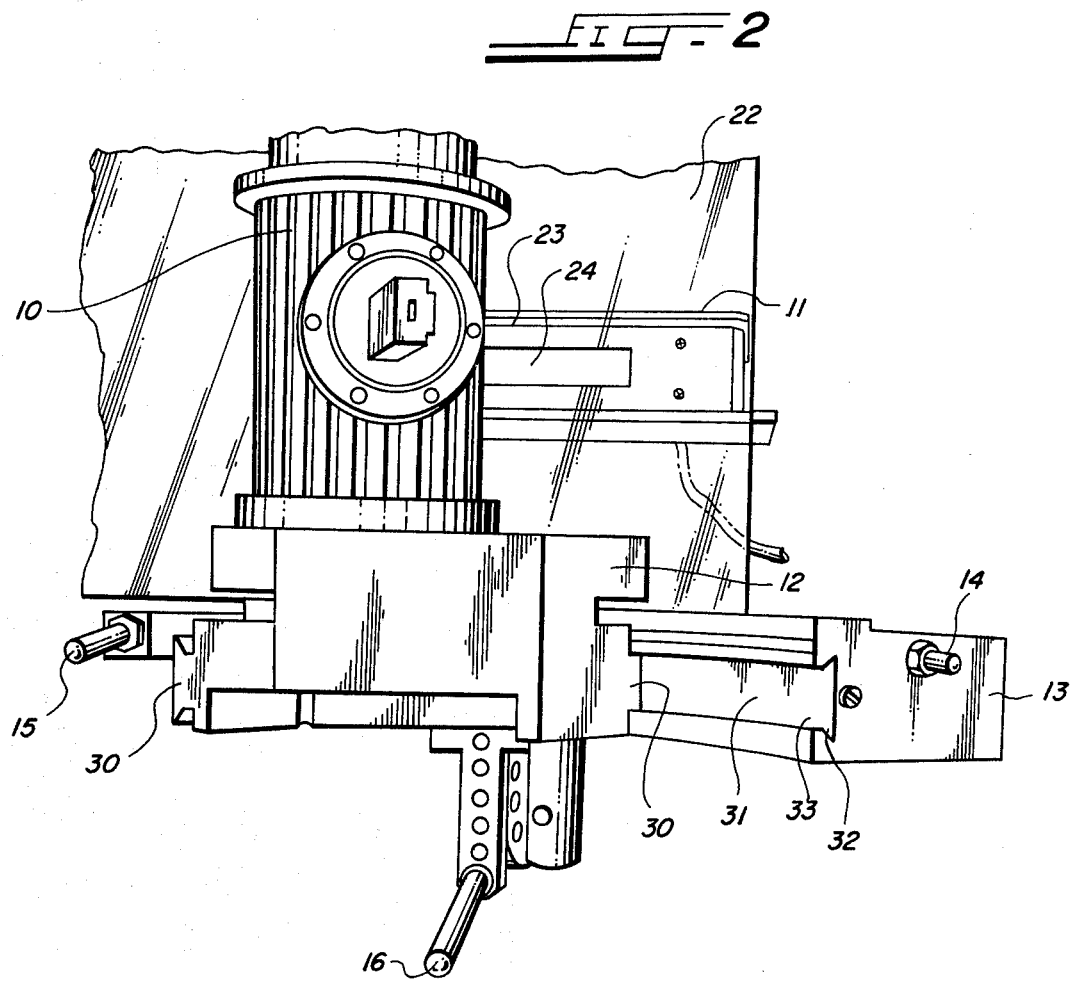
FIG. 2 is a front perspective view of the apparatus of FIG. 1.

A preferred embodiment of the apparatus of the present invention is illustrated in FIGS. 1 and 2. An X-ray source or tube 10 and a position-sensitive X-ray detector 11 are mounted on a movable platform 12 carried by a base 13. Three positioning probes 14, 15, 16 extend forwardly of the base 13 to engage a support surface 17 aligned with the principal surface 18 of a metal plate being tested for residual stress. The total weight of the apparatus shown is only 11 kg.

A handle 20 is affixed to a rear aspect of the base 13 for positioning the apparatus. A strap 21 affixed to the base 13 and looped around the neck of an operator steadies the apparatus in position while measurements are being made with the detector 11. A clear plastic shield 22 having a thickness of 0.8 cm is mounted on the platform rearwardly of the X-ray tube 10 to reduce exposure of the operator to scattered radiation. The shield 22 defines a slit 23 coinciding with a window 24 of the detector 11.

The X-ray tube 10 is a miniature 50 kV-2mA tube having a solid-state power supply obtained from Watkins-Johnson Co. of Palo Alto, Calif. The X-ray tube weighs only 2.3 kg and it utilizes a non-intercepting grid electron gun to focus the electron beam so that less power is necessary (and less heat generated) to produce an equivalent X-ray flux compared with a conventional sealed X-ray tube. The X-ray tube has a spotfocus and the target is mounted such that the target normal is 24° from the electron beam, giving a take-off angle of 24°.* Using similar sample-to-detector distances, the miniature Cr X-ray tube 10 employed herein gave a diffracted intensity at the detector 11 which was 1.2 times greater than a standard Picker Cr X-ray tube operated at 50 kV and 11mA.

*The target is tilted about an axis parallel to the diffraction plane, rather than around an axis perpendicular to this plane as in a normal tube.

Figure 4:
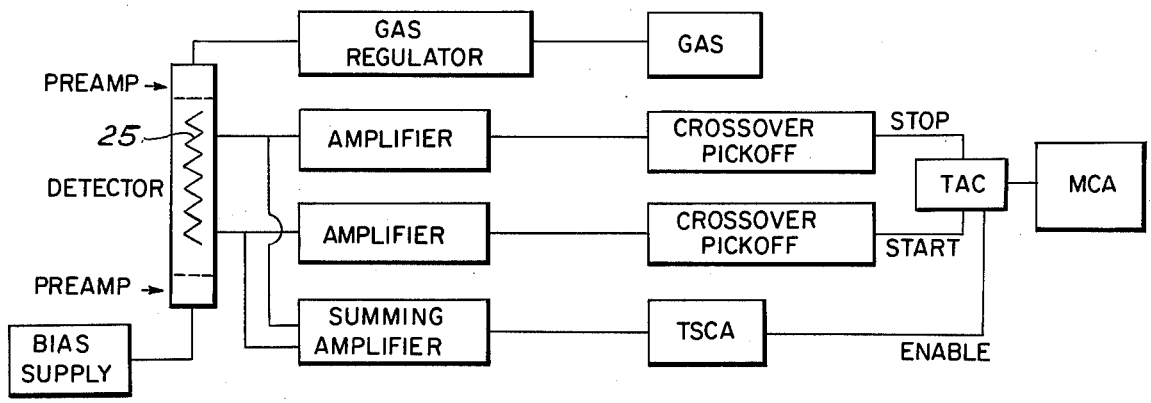
FIG. 4 is a schematic diagram of the electronics for the position determination circuit and parallel energy discrimination circuit of the position-sensitive X-ray detector of the invention.

In a preferred embodiment of the invention the X-ray detector 11 is a linear, position-sensitive proportional counter of the type described by C. J. Borkowski and M. K. Kopp in their U.S. Pat. No. 3,483,377 issued Dec. 9, 1969. To the extent not inconsistent with the present invention, the disclosure of said patent is incorporated herein. The particular instrument found to have greatest utility includes an aluminum casing with a window 24 having an active length of 10 cm, although the bulk housing is 20 cm long. The counting gas is Ar3% $CO_2$ maintained at a pressure of approximately 80 psi. The anode or collecting element 25 is a quartz fiber wire having a resistance of approximately 100,000 ohms per millimeter. Electronics of the instrument are outlined schematically in FIG. 4.

X-rays entering the detector window 24 cause a multiplicity of ionizing events in the counting gas. Ionized particles resulting from these events migrate to the collecting element or wire 25 where they induce first and second voltage pulses. The rise times of the two pulses induced by the ionizing event and collected at first and second ends of the anode are dependent upon the RC value of the detector, where R is the resistance of the anode wire and C is the effective capacitance as seen by the pulse. After amplification and pulse shaping (two differentiations and one integration) two crossover pickoff detectors are used to give timing information related to the rise time of each pulse. The difference in the rise time of the pulse at each end of the detector is directly related to the position of the event, enabling a time to amplitude converter (TAC) to measure the time difference between the two pulses and deliver a signal whose amplitude is proportional to the position of the event. This signal is output to a storage device, usually a multichannel analyzer. Energy discrimination is provided by a timing single channel analyzer (TSCA) whose logical pulse must be presented to the TAC for the amplitude signal to be output to the storage device.

The present invention does not require either $2\theta$ movement of the detector or a preliminary scan to locate diffraction peaks. Data are stored in the multichannel analyzer and automatically transferred to a minicomputer or microcomputer for mathematical manipulation. Calibration of the instrument is necessary only once at fixed electronic settings to convert channel numbers to °$2\theta$. Calibration is obtained with any stress free sample having known lattice parameters. The instrument used in accumulating the data of Table 1 was calibrated with an annealed Fe sample and a stress free steel, SAE designation 1090. The profiles from both specimens give excellent $K_1 - K_2$ separation which is used to calculate a linear calibration constant. Both samples give identical constants of 0.021° $2\theta$ channel.

The platform 12 of the apparatus is provided with an arcuate bracket 30 which extends rearwardly and appears generally dove-tailed in transverse cross-section (see FIG. 2). This bracket 30 is rotatably coupled within a corresponding elongated arcuate glide channel 31 formed in the base and opening forwardly thereof. The channel 31 includes an elongated hollowed out inner chamber 32 adjacent the base 13 and an elongated narrow passageway 33 communicating with the inner chamber and opening forwardly of the base 13.

If desired, the apparatus can be moved inwardly and outwardly with respect to the sample surface 18 in order to optimize the sample-to-detector distance. In the preferred embodiment illustrated in FIGS. 1–3 this distance 40 is 21.0 cm. This distance is measured by a Starrett micrometer 45 mounted on the platform 12 adjacent the X-ray source 10. The micrometer 45 is shown in FIG. 1 but has been removed for convenience of illustration in FIG. 2.

It has been calculated that the sample-to-detector distance 40 should be about 8 cm. under typical operating conditions in order to optimize precision. However, the large diameter of the X-ray tube 10 prevents reduction of the sample-to-detector distance 40. The reduction in precision thereby introduced is calculated to be small compared with other errors inherent in the apparatus.

Figure 3:
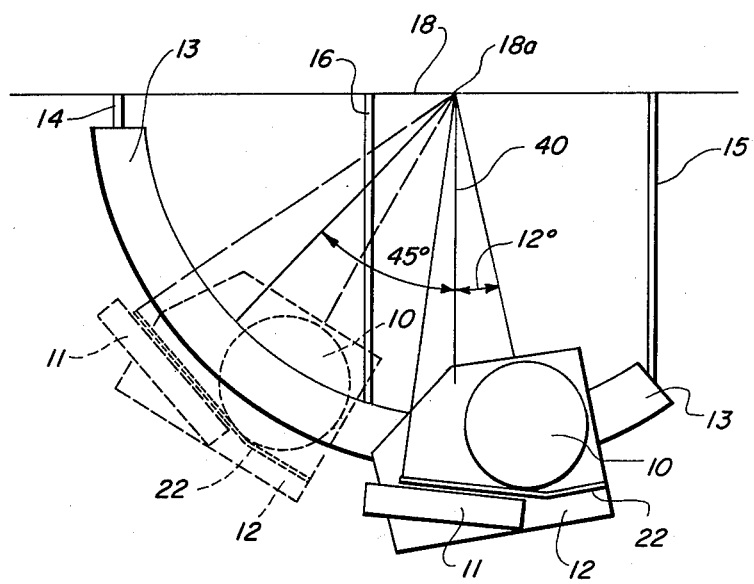
FIG. 3 is a schematic top plan view of the apparatus of FIG. 1, positioned at angles of $\Psi = 0$ and $105 = 45°$ with respect to a principal surface of a metal sheet.

In contrast with the usual laboratory practice of rotating a metal specimen to obtain a $\Psi$-tilt, the apparatus of the invention is rotated about a principal surface 18 of the metal specimen being tested. The angle $\Psi$ mentioned in FIG. 3 is defined as the angle between a normal to the diffraction plane and a normal to the principal surface 18 of the substance being tested. In the portion of FIG. 3 shown in solid lines $\Psi = 0$ and in the dashed line portion of FIG. 3 the apparatus has been rotated by an angle $\Psi = 45°$. the apparatus is provided with stop means or stop latches (not shown) to ensure precise measurement of the angle $\Psi$. For the results reported in Table I the angle of rotation $\Psi$ was 45°.

As illustrated in FIG. 3, the three positioning probes 14, 15, 16 are located on the base 13 in positions such that at $\Psi = 0$ the primary X-ray beam is displaced off normal to the sample surface 18 by 12°, corresponding to an expected diffraction angle of 156° $2\theta$. This is a typical diffraction angle for Fe and it is also suitable for Al because the detector 11 has a useful detection range of about 10°. The X-ray tube 10 is positioned to intersect the sample surface 18 at a point 18a corresponding to an axis of rotation of the platform 12 around the base 13.

Figure 5:
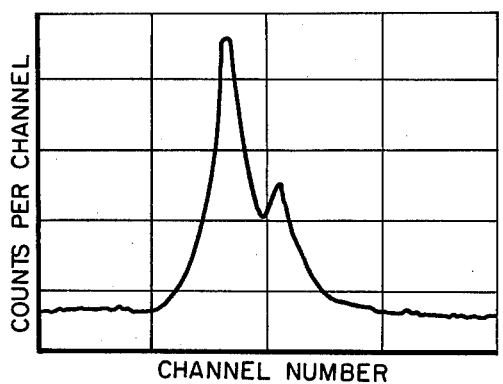
FIG. 5 is a front elevational view of a cathode ray tube screen displaying a typical X-ray diffraction peak obtained from a steel specimen by the method of the invention.
Figure 6:
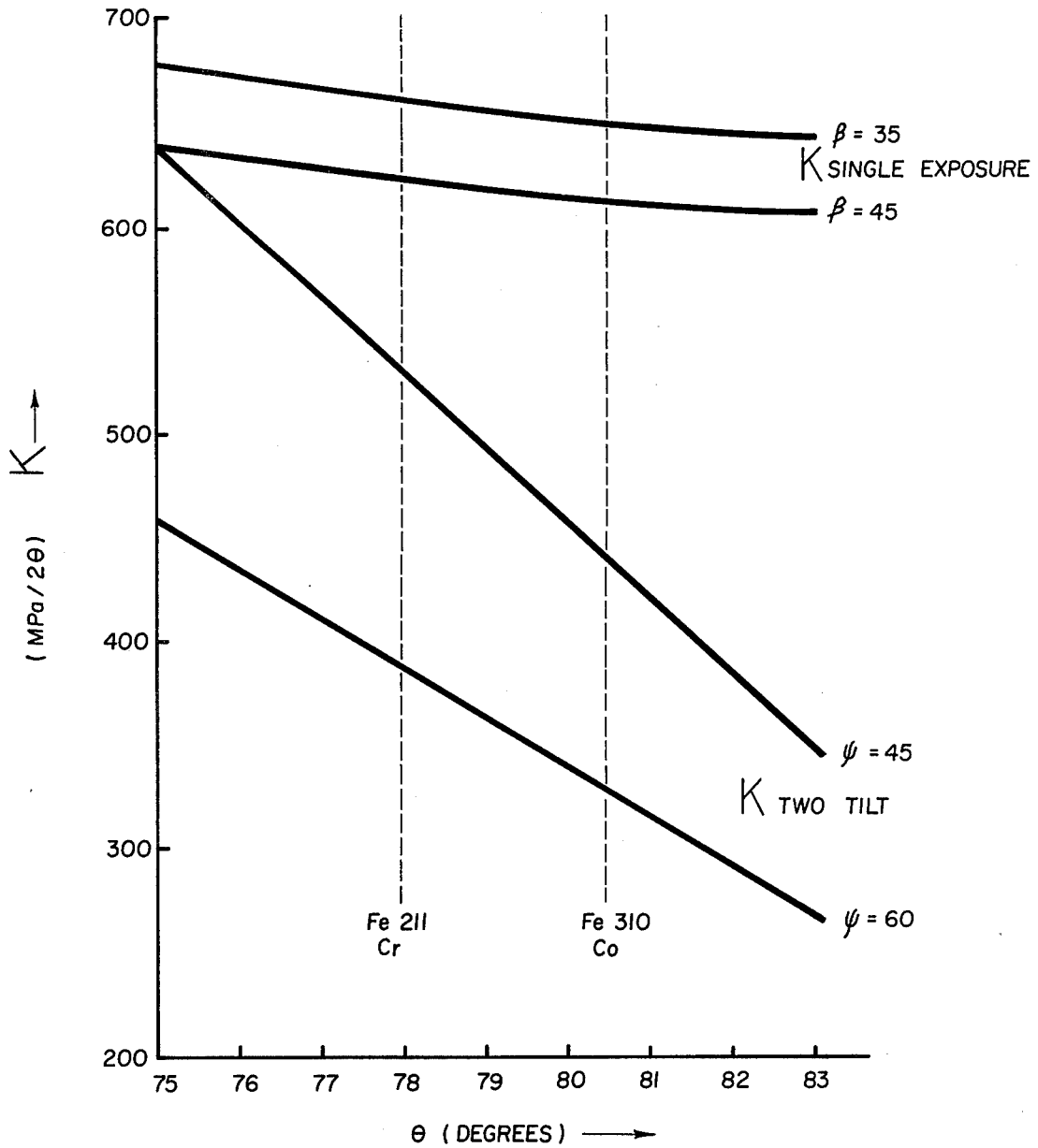
FIG. 6 is a graph of stress constant $k$ as a function of diffraction angle for the single exposure method of Bens Pat. No. 3,934,138 and for the two tilt method of the invention.

A typical diffraction profile appearing on a cathode ray screen output from the multi-channel analyzer is shown in FIG. 5.

The portable residual stress detector of FIGS. 1 and 2 is designed to perform measurements on large, flat surfaces. In order to test the accuracy of the device, three steel samples previously tested with a diffractometer were analyzed. The samples were mounted on a large, flat steel plate 17 so that a principal surface 18 of each was flush with the surface of the plate, as shown in FIG. 1. This was accomplished by milling into the plate a recess equal to the thickness of each sample. Probes 14, 15, 16 of the device were then abutted against the plate 17 and each sample was tested.

Results of tests on the three samples are reported below in Table I. Column 2 shows the total measurement time for each sample. Column 3 shows the average stress found in each sample on a diffractometer. Column 4 shows the average stress over five measurements using the portable analyzer of the invention with the observed error of one standard deviation shown in column 5 and the average counting statistical error in Column 6.

TABLE I
REPLICATE MEASUREMENT USING PORTABLE RESIDUAL STRESS ANALYSER
(5 measurements)

| 1 | 2 | 3 | 4 | 5 | 6 |
|---|---|---|---|---|---|
| Sample | Time (sec) | Diffractometer* MPa (psi) | Mpa (psi) | Observed error 5 tests MPa (psi) | Statistical error 5 tests MPa (psi) |
| 1090-1 | 10 | +31.6(+4580) | −11.6(−1682) | ±25.4 (±3684) | ±19.5 (±2828) |
| 1045-3 | 20 | −699.2(−101410) | −703.4(−102016) | ±28.3 (±4100) | ±29.4 (±4264) |
| 1045-2 | 20 | −397.1(−57596) | −396.4(−57491) | ±42.7 (±6193) | ±36.7 (±5315) |

In all cases, the measured stress was within two standard errors (as given by the counting statistics) of the value measured on the diffractometer, with the average value being quite close. The times of analysis reported in Column 2 indicate that the device is capable of extremely rapid measurements. A total measurement time of 20 seconds (for both tilts) gives acceptable errors of ± 36.7 Mpa (±5315 psi) on the broadest profiled sample. For the sharp-profiled 1091-2 sample a total measurement time of only four seconds gave a statistical counting error of ±34 MPa. The calculated counting time for a sample-to-detector distance of 21 cm and an error of ±40 MPa (±5800 psi) is 24 seconds, quite close to the actually observed time.

A crude test was made of errors introduced by displacement of the detector. The X-ray tube 10 and detector 11 were mounted on a track which moved inwardly and outwardly with respect to the specimen 18. The sample-to-detector distance could be varied in this way by 5 cm. Because the Ψ axis remained fixed, this motion did not introduce any Ψ-axis missetting or sample displacement. These large movements did require recalibration of the detector 11, however.

When the detector was moved forward by 2.5 cm (reducing the sample-to-detector distance to 18.5 cm), a total counting time of 16 seconds gave an average error of ±38.6 MPa (±5600 psi) over three repeated stress measurements. After increasing the sample-to-detector distance by 2.5 cm. to 23.5 cm., a counting time of 30 seconds gave an average error of ±41.6 MPa (±5950 psi). These values compare quite closely with calculated values for an optimum sample-to-detector distance of about 8 cm. If size of the X-ray tube 10 can be decreased, the sample-to-detector distance 40 can also be lowered to a value closer to the optimum.

Errors introduced by possible displacement of the sample surface 18 have also been tested. The 1045-2 sample was moved forward by 1mm and 2mm using spacers and three repeated stress measurements made at each sample displacement setting for a total counting time of 40 seconds. The average value of the measured stress was −407.2 MPa (−59060 psi) and −420.8 MPa (−61035 psi) at 1mm and 2mm displacements respectively. The expected error for a 1mm displacement (R=21 cm) is approximately −10 MPa (−1400 psi) using a stress constant of 600 MPa (87020 psi). These values of stress are reasonable and indicate that small displacements of the sample introduce only minor errors.

In order to enhance mobility of the apparatus of the invention, the electronics and computer system for analysis of detector data must be miniaturized. Using presently available technology it is believed that the electronics for the PSD and a hardware system for data storage and manipulation can be packaged in a rectangular box measuring about 50 × 50 × 20 cm. This box plus the solid state power supply of the X-ray tube (50 × 50 × 15 cm) would constitute a fixed cabinet weighing about 35 kg. Although the instrument described herein weighs 11 kg, this weight can easily be reduced to about 7 kg by lightening the base 13 and shielding for the X-ray tube 10.

The foregoing description of our invention has been made with reference to a particular preferred embodiment. Persons skilled in the art will understand that numerous changes, alterations and modifications can be made therein without departure from the spirit and scope of the invention as set forth in the following claims.

What is claimed is:

1. A quick and precise method for determination of residual stress in crystalline substances by locating a plurality of X-ray diffraction peaks with a single X-ray detector and without diffractometer shifting of said X-ray detector, said method comprising the steps of
    (a) focusing an X-ray source to direct X-rays at an angle with respect to a principal surface of a crystalline substance;
    (b) diffracting said X-rays;
    (c) receiving X-rays emanating from the substance in a single position-sensitive X-ray detector responsive to said X-rays to produce a multiplicity of ionizing events clustered about a position corresponding to a diffraction peak, said single position-sensitive X-ray detector including a collecting element providing first and second voltage pulses at respective first and second output ends of said detector in response to ionized particles, said first and second voltage pulses each having a rise time proportional to respective distances between the position of an ionizing event occurring within said detector and said first and second output ends of the collecting element;
    (d) locating a diffraction peak of said X-rays correlated with a first diffraction angle by determining rise times of the first and second voltage pulses produced in said collector, thereby indicating a position of an ionizing event occurring within said detector corresponding to a first diffraction peak;
    (e) varying a preselected angle the relationship between said X-ray source and said principal surface of the crystalline substance; and
    (f) locating a second diffraction correlated with a second diffraction angle by repeating steps (a) through (d), step (c) being performed with the same position-sensitive X-ray detector used for locating said first diffraction peak, a difference between the first and second diffraction angles being indicative of magnitude and direction of residual stress in the substances.

2. Apparatus for quick and precise determination of residual stress in crystalline substances by locating a plurality of X-ray diffraction peaks with a single X-ray detector and without diffractometer shifting of said detector, comprising a platform;

an X-ray source carried by said platform;

a single position-sensitive X-ray detector carried by said platform, said detector defining an elongated window adapted to receive X-rays therethrough, and including first and second output ends and a collecting element providing first and second voltage pulses at respective said first and second output ends in response to ionized particles received through said window; and a base supporting said platform and including guide means attached to said platform for maintaining a constant distance between said X-ray detector and a principal surface of a crystalline substance irrespective of angular shifting of said platform with respect to said principal surface, stop means for securing said platform in any of a plurality of preselected rest positions corresponding to a plurality of preselected angular relationships between said X-ray source and said principal surface, and positioning means for maintaining said base in fixed relationship with said principal surface.

3. The apparatus of claim 2, wherein said guide means comprises, in combination, an elongated arcuate glide channel formed integrally in said base, and a bracket affixed to said platform and rotatably coupled with said channel for arcuate movement around said principal surface.

4. The apparatus of claim 3, wherein said channel includes an elongated hollowed out inner chamber and an elongated passageway narrower than said inner chamber and communicating therewith, said passageway opening radially inwardly of the base.

5. The apparatus of claim 2, wherein said positioning means comprises three probes adapted to extend between said base and a support surface aligned with the principal surface of the crystalline substance, thereby to stabilize said base against said support surface and to preclude misalignment of said platform.

6. The apparatus of claim 2, wherein said single position-sensitive X-ray detector is filled with an ionizable gas, and said collecting element comprises a quartz fiber wire.

7. The apparatus of claim 6, wherein said ionizable gas comprises about 97 parts argon and about 3 parts carbon dioxide maintained at a pressure of about 80 psi.

* * * * *